US006121327A

United States Patent [19]

Tsuzuki et al.

[11] Patent Number: 6,121,327

[45] Date of Patent: Sep. 19, 2000

[54] CONTACT LENS DISINFECTING SOLUTION

[75] Inventors: Akira Tsuzuki; Osamu Mori, both of Nagoya; Hideshi Nomura, Bisai, all of Japan

[73] Assignee: Menicon Co., Ltd., Nagoya, Japan

[21] Appl. No.: 09/316,598

[22] Filed: May 21, 1999

[30] Foreign Application Priority Data

May 22, 1998 [JP] Japan .................................. 10-141692
Apr. 27, 1999 [JP] Japan .................................. 11-119835

[51] Int. Cl.[7] ..................................................... A61K 31/14

[52] U.S. Cl. ............................................ 514/642; 514/912

[58] Field of Search ...................................... 514/642, 912

[56] References Cited

U.S. PATENT DOCUMENTS 5,453,435 9/1995 Raheja et al. ........................... 514/402

FOREIGN PATENT DOCUMENTS 10-108899 4/1998 Japan .
11-130602 5/1999 Japan .
WO 95/01414 1/1995 WIPO .
WO 97/28827 8/1997 WIPO .

*Primary Examiner*—Zohreh Fay
*Attorney, Agent, or Firm*—Wall Marjama Bilinski & Burr

[57] ABSTRACT

A contact lens disinfecting solution which does not include protease, wherein an organic nitrogen disinfectant and 0.01–5 w/v % of at least one polyol are contained in an aqueous medium.

12 Claims, No Drawings

CONTACT LENS DISINFECTING SOLUTION

The present application is based on Japanese Patent Applications Nos. 10-141692 filed May 22 and 11-119835, filed Apr. 27, 1999, the contents of which are incorporated hereinto by reference.

BACKGROUND OF THE INVENTION

1. Field of the Art

The present invention relates to an improvement of a disinfecting solution for contact lenses. In particular, the invention is concerned with such a disinfecting solution which exhibits an excellent disinfecting or preservative effect while assuring significantly enhanced safety to the eyes of the lens wearer. Further, the present invention relates to the disinfecting solution which permits the contact lenses to be directly worn on the eyes of the lens wearer, without a need of rinsing of the lenses after they are treated with the disinfecting solution.

2. Discussion of the Related Art

Generally, contact lenses are classified into hydrophobic contact lenses and hydrophilic or hydrated contact lenses, or hard contact lenses and soft contact lenses. These contact lenses may be soiled with deposits such as protein and lipid during wearing of the contact lenses on the eyes, which deposits derive from tear fluid and lipid of the eyes. These deposits adhering to the contact lenses deteriorate the wearing comfort of the contact lenses as felt by the lens wearer, lower the eyesight of the lens wearer, and cause various troubles with the eyes such as hyperemia of the conjunctiva. In view of these problems, the contact lenses which have been removed from the eyes need to be cleaned for safe and comfortable wearing thereof.

Besides the cleaning treatment described above, the contact lenses which have been removed from the eyes need to be disinfected, and then stored in a suitable storing liquid for the purpose of preventing proliferation of microorganisms such as bacteria and molds on the lens surfaces during storage thereof. The procedure for treating the contact lenses such as cleaning, disinfecting and storing is indispensable for safe wearing of the contact lenses on the eyes of the lens user.

The procedure for treating the contact lenses is, however, considerably cumbersome, requiring several kinds of liquid agents such as a cleaning solution, a disinfecting solution, and a storing solution. Accordingly, it is troublesome and costly for the contact lens users to treat and maintain the contact lenses.

For solving the above problem, various multi-purpose contact lens liquid agents are commercially available at home and abroad. These multi-purpose liquid agents are obtained by adding, to a storing solution, a surface active agent and a disinfectant. The contact lenses can be cleaned, rinsed, disinfected, and stored by using such a single liquid agent.

Although various compounds are conventionally proposed as the disinfectant to be included in those liquid agents, these compounds need to be used in relatively high concentrations for permitting the liquid agents to exhibit a practically sufficient disinfecting effect. For instance, biguanide derivatives whose typical example is polyhexamethylene biguanide (PHMB) have been recently attracting attentions as the disinfectant. The biguanide derivatives are one example of a high-molecular organic disinfectant containing nitrogen groups (organic nitrogen disinfectant), and have a superior disinfecting property as compared to the other disinfectants. A recent study, however, reveals that the biguanide derivatives alone do not provide a sufficiently high disinfecting or preservative effect. Accordingly, for assuring a practically useful disinfecting effect, it is necessary to increase the amount of the biguanide derivatives to be included in the contact lens liquid agents. The biguanide derivatives if used in high concentrations, however, are toxic to the eyes, and irritate the mucous membranes of the eyes to cause inflammation, giving rise to a problem of insufficient safety. In view of this, various studies have been made to provide a contact lens liquid agent capable of exhibiting a higher disinfecting effect while reducing the required amount of the biguanide derivatives.

For instance, JP-A-6-321715 discloses a contact lens disinfecting and storing solution which uses the biguanide derivative together with a boric acid buffer. The disclosed solution has a low degree of toxicity to the eyes while having a high level of antimicrobial activity. JP-A-6-504044 discloses a contact lens disinfecting composition which includes the biguanide derivative in combination with a tris buffer. The disclosed composition has an excellent disinfecting property and gives substantially no irritation to the eyes. Both of the disclosed solution and composition, however, are not considered to have satisfactorily high disinfecting efficacy.

JP-A-52-110055 discloses a contact lens storing solution obtained by dissolving in an organic alcohol or a non-aqueous solvent, a disinfectant formed of an ene-diol compound, in combination with a catalytic metal compound (catalyst). The proposed storing solution suffers from problems such as a low disinfecting capability due to the use of the ene-diol compound as the disinfecting component, and insufficient safety resulting from the use of the metallic catalyst.

JP-A-8-224288 and JP-A-9-38180 disclose a method of simultaneously cleaning and disinfecting contact lenses, by using a cleaning and disinfecting solution which contains an effective amount of protease, a predetermined amount of glycerin, water, and 60–80 w/v % or 15–60 w/v % of propylene glycol. In the disclosed treating solution, the concentration of propylene glycol is considerably high, undesirably increasing the osmotic pressure of the treating solution, whereby the material of the contact lenses may be adversely affected. Since the treating solution contains the protease, the contact lenses which have been treated with the treating solution need to be rinsed with a suitable rinsing solution before the contact lenses are worn on the eyes of the lens user. If the contact lenses are worn on the eyes without being rinsed, the treating solution remaining on the contact lenses may irritate the eyes.

JP-A-6-194610 discloses a method of cleaning, storing and disinfecting contact lenses, by using a treating solution which contains an effective amount of Bacillus-derived serine protease and a metal chelating agent, wherein the serine protease is stabilized by a boric acid and/or borax. The publication suggests inclusion of 0.5–2 w/v % of polyhydric alcohol in the treating solution, merely for improving the stability of the enzyme (serine protease) in the treating solution. Since the disclosed treating solution contains the serine protease (proteolytic enzyme), the contact lenses which have been treated with the treating solution need to be sufficiently rinsed with a rinsing solution before the contact lenses are worn on the eyes of the lens wearer. When the contact lenses are worn on the eyes without being rinsed, the treating solution remaining on the contact lenses may cause various troubles with the eyes such as keratitis and conjunctivitis.

SUMMARY OF THE INVENTION

It is therefore a first object of the present invention to provide a contact lens disinfecting solution which exhibits an excellent disinfecting or preservative effect while assuring sufficiently high safety to the eyes of the lens wearer, and which does not include a large amount of an organic disinfectant containing nitrogen groups (organic nitrogen disinfectant) as a disinfecting component in the disinfecting solution.

It is a second object of the present invention to provide a contact lens disinfecting solution which eliminates a step of rinsing the contact lenses with a rinsing solution, so that the contact lenses can be directly worn on the eyes of the lens user immediately after the contact lenses are treated with the disinfecting solution.

As a result of an extensive research made by the inventors of the present invention, it has been found that a combined use of a suitable organic disinfectant containing nitrogen groups (organic nitrogen disinfectant) as a disinfecting component and a predetermined amount of a polyhydric alcohol or polyol effectively enhances or intensifies the antimicrobial activity to be exhibited by the organic nitrogen disinfectant. Accordingly, the disinfecting solution is capable of exhibiting a sufficiently high disinfecting effect by including the disinfectant in a concentration much lower than that in the conventional disinfecting solution.

The above objects of the present invention may be attained according to a principle of the invention, which provides a contact lens disinfecting solution which does not include protease, wherein an organic nitrogen disinfectant and 0.01–5 w/v % of at least one polyol are contained in an aqueous medium.

In the present contact lens disinfecting solution described above, the antimicrobial activity of the suitably selected organic nitrogen disinfectant is effectively intensified owing to the combined use with the predetermined amount of polyhydric alcohol or polyol. Accordingly, the required amount of the disinfectant to be included in the present disinfecting solution can be reduced since the concentration of the disinfectant required for providing substantially the same disinfecting or preservative effect as the conventional disinfecting solutions can be lowered. Thus, the present disinfecting solution assures appreciably enhanced safety to the eyes of the lens user.

In one preferred form of the present invention, the disinfecting solution has a pH of 5–8 and an osmotic pressure of 250–350 mOsm/kg. The disinfecting solution having the pH and the osmotic pressure held within the respective specified ranges assures high safety to the eyes.

In another preferred form of the present invention, the polyol is contained in an amount of 0.1–3 w/v %. As the polyol, it is preferable to use at least one of a diol and a triol which have a principal chain constituted by an alkylene group having 2–8 carbon atoms. It is preferable to use a diol and/or a triol whose principal chain is constituted by an alkylene group having 2–5 carbon atoms, for providing a higher degree of disinfecting effect. To prevent swelling of the contact lenses while the lenses are treated with the disinfecting solution, it is preferable to use a diol and/or a triol whose principal chain is constituted by an alkylene group having 4–8 carbon atoms.

In still another preferred form of the present invention, the organic nitrogen disinfectant is contained in the aqueous medium in an amount of 0.00001–0.1 w/v %. The organic nitrogen disinfectant preferably comprises at least one compound selected from the group consisting of quaternary ammonium compounds and polymerization products thereof, biguanide compounds and polymerization products hereof, and polymerization products of at least one of the quaternary ammonium compounds and at least one of the biguanide compounds.

In yet another preferred form of the present invention, the contact lens disinfecting solution further contains at least one of a nonionic surfactant, a nonionic or a cationic thickener, a buffer, and a chelating agent, so that each of these additional components exhibits an intended function. For instance, the disinfecting solution has a cleaning activity by inclusion of the nonionic surfactant therein. The nonionic or cationic thickener gives suitable viscosity to the disinfecting solution, so that the contact lenses are smoothly slidable on the palm or between the fingers of the lens user when the lenses are cleaned by finger-rubbing with the present disinfecting solution, to thereby facilitate the cleaning of the contact lenses. Further, the nonionic or cationic thickener prevents the deposits which have been removed from the contact lenses from adhering back to the lenses, and renders the contact lenses hydrophilic. In addition, the nonionic or cationic thickener is effective to improve the wearing comfort of the contact lenses as felt by the lens user when the lenses are directly worn on the eyes without being rinsed after the lenses are treated with the disinfecting solution. The buffer is effective to stabilize the pH of the disinfecting solution, avoiding troubles such as irritation to the eyes. The chelating agent protects the contact lenses from being adversely influenced by metal ions due to its chelate effect.

As the buffer to be included in the present disinfecting solution, it is preferable to use hydroxyalkylamine or its derivatives. In particular, bis(2-hydroxyethyl)iminotris (hydroxymethyl)methane is preferable for removing deposits derived from the tear fluid.

As the nonionic or cationic thickener, it is preferable to use sugar derivatives, especially cellulose derivatives since these derivatives do not adversely affect the properties of the contact lenses even if the contact lenses are treated with the disinfecting solution which has been stored for a relatively long period of time.

DETAILED DESCRIPTION OF THE PREFERRED EMBODIMENT

In the contact lens disinfecting solution according to the present invention, a suitable organic disinfectant containing nitrogen groups (organic nitrogen disinfectant) is included together with a predetermined suitable amount of polyhydric alcohol or polyol in water as a medium, so that the disinfecting solution exhibits a synergistic disinfecting or preservative effect. The present disinfecting solution is capable of disinfecting contact lenses in a simplified manner owing to the synergistically enhanced disinfecting or preservative effect. Further, the present disinfecting solution permits the contact lenses to be directly worn on the eyes of the lens user without having to be rinsed with a rinsing solution, after the lenses have been treated with the disinfecting solution.

The organic nitrogen disinfectant used in the present contact lens disinfecting solution not only has the disinfecting activity, but also provides the synergistic disinfecting effect by the combined use with the polyol. Further, the organic nitrogen disinfectant to be used is not adsorbed on the contact lenses, and has high compatibility with the material of the contact lenses, eliminating a risk of causing various eye troubles such as an allergy. The organic nitrogen disinfectant is generally used in a concentration of 0.00001–0.1 w/v %, preferably 0.00005–0.05 w/v %, for exhibiting an effective disinfecting or preservative activity. If the concentration of the organic nitrogen disinfectant is lower than the lower limit of 0.00001 w/v %, it is difficult to obtain the intended high disinfecting or preservative effect. The disinfecting or preservative effect exhibited by the organic nitrogen disinfectant does not significantly increase with an increase in the concentration above the upper limit of 0.1 w/v %. On the contrary, the inclusion of the organic nitrogen disinfectant in a concentration exceeding the upper limit may adversely affect the human body due to adsorption of the disinfectant on the lens surfaces and increased toxicity, thereby causing a problem of insufficient safety.

While any known organic nitrogen disinfectants may be used in the present invention, it is preferable to use the organic nitrogen disinfectant which comprises at least one compound selected from the group consisting of quaternary ammonium compounds and polymerization products thereof, biguanide compounds and polymerization products thereof, and polymerization products of at least one of the quaternary ammonium compounds and at least one of the biguanide compounds. In addition, any known amphoteric surfactants including the organic nitrogen may be preferably used.

Any suitable biguanide compounds (including salts thereof) and polymerization products of the biguanide compounds known as the disinfectant may be used in the present invention, provided that they are ophthalmically acceptable. For instance, polyhexamethylene biguanide or chlorhexidine is preferably used. It is particularly recommended to use an ophthalmically acceptable biguanide derivative represented by the following formula (1):

(1)

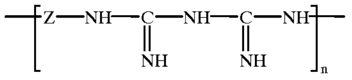

wherein, Z represents an organic divalent group which may be the same or different throughout the polymer, and n represents an integer of not smaller than 1.

A preferable example of such a biguanide derivative is represented by the following formula (2), and a more preferable example is represented by the following formula (3):

(2)

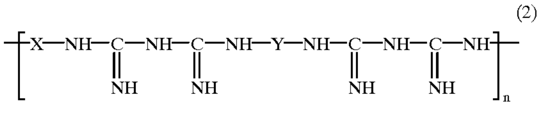

wherein, X and Y represent respective different ones of a polymethylene group having 2–18 carbon atoms and a polyoxyalkylene group, and n represents an integer of not smaller than 3.

wherein m represents an integer of 2–4, and n represents an integer of 1–500.

In particular, the polyhexamethylene biguanide (PHMB) is preferably used as the biguanide derivative in the present invention. If the PHMB is used as the disinfecting component, the amount of the PHMB required to be included in the present disinfecting solution can be made relatively small, e.g., generally in a range of 0.01–100 ppm, preferably 0.1–10 ppm.

Examples of the quaternary ammonium compounds (including salts thereof) and polymerization products of the quaternary ammonium compounds used as the organic nitrogen disinfectant include known cationic surfactants, polycationic surfactants such as a condensation product of diamines and dihalogen compounds as disclosed in JP-B2-2550036, and benzalkonium halide. These compounds are suitably used as the organic nitrogen disinfectant, as long as they are ophthalmically acceptable.

One typical example of the cationic surf actant is an alkyl ammonium salt such as a tetraalkyl ammonium salt. Examples of the tetraalkyl ammonium salt include: alkyltrimethylammonium chlorides such as octadecyl trimethylammonium chloride, dioleyldimethylammonium chloride, dodecyltrimethylammonium chloride, didecyldimethyl ammonium chloride, acylalkyltrimethylammonium chloride, tetradecyltrimethylammonium chloride, and hexadecyltrimethyl ammonium chloride; octadecyltrimethylammonium bromide; dioleyldimethylammonium bromide; dodecyltrimethylammonium bromide; didecyldimethylammonium bromide; acylalkyltrimethyl ammonium bromide; tetradecyltrimethylammonium bromide; and hexadecyltrimethylammonium bromide. Further, trialkylbenzyl ammonium salts such as octadecyldimethylbenzylammonium chloride and octadecyldimethylbenzylammonium bromide may also be used as the cationic surfactant. Any other ophthalmically acceptable cationic surfactants may also be used. For instance, quaternary salts of alkylhydroxy alkylimidazoline whose typical example is hydroxyethyl alkylimidazoline chloride, alkylisoquinolinium salts whose typical example is alkylisoquinolinium bromide, alkylpyridinium salts, and amideamines may be used, provided that they are ophthalmically acceptable.

One typical example of the amphoteric surfactant used as the organic nitrogen disinfectant in the present invention is alkylglycine. Examples of the alkylglycine include: alkylaminoethylglycine.hydrochloride salts such as dodecyl (aminoethyl)glycine.hydrochloride salt; alkyl di(aminoethyl)glycine.hydrochloride salts such as tetradodecyl di(aminoethyl)glycine.hydrochloride salt and lauryl di(aminoethyl)glycine.hydrochloride salt; alkyl poly (aminoethyl)glycine.hydrochloride salts such as octyl poly (aminoethyl)glycine.hydrochloride salt; dodecyl guanidine-.hydrochloride salts; and di(octylaminoethyl) glycine.hydrochloride salts. Any other ophthalmically acceptable cationic surfactants may also be used. For instance, alkylbetaines such as dimethylalkylbetaine, imidazolines such as alkylimidazoline, amidebetaines, acyl hydrolytic collagen peptide salts, and betaine acetate may be used as long as they are ophthalmically permissible.

(3)

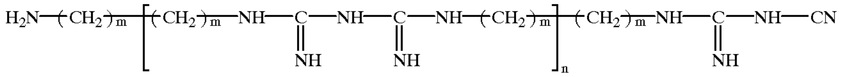

The present contact lens disinfecting solution includes the organic nitrogen disinfectant which includes at least one compound selected from the group consisting of the quaternary ammonium compounds and polymerization products thereof, the biguanide compounds and polymerization products thereof, and polymerization products of at least one of the quaternary ammonium compounds and at least one of the biguanide compounds, so that the present contact lens disinfecting solution can exhibit the intended disinfecting or preservative effect.

The polyol used in combination with the above-described organic nitrogen disinfectant enhances the disinfecting activity of the organic nitrogen disinfectant. Owing to the combined use of the organic nitrogen disinfectant and the polyol, the present contact lens disinfecting solution can exhibit a remarkably increased preservative or disinfecting effect even when the amount of the organic nitrogen disinfectant to be included is significantly reduced.

The polyol to be used in the present invention is suitably selected from any known ophthalmically acceptable alcohols having at least two hydroxyl groups. Particularly preferred are diols such as alkylene glycol and its derivatives, and triols such as glycerin and its derivatives. Particularly preferably used are at least one of diols and triols, which have a principal chain constituted by a saturated alkylene group having 2–8 carbon atoms, especially 2–5 carbon atoms, for increasing the disinfecting effect. Examples of such diols and triols include ethylene glycol, propylene glycol, butylene glycol and pentylene glycol. In order to prevent the contact lenses from being swollen with the disinfecting solution, it is preferable to use at least one of diols and triols whose principal chain is constituted by a saturated alkylene group having 4–8 carbon atoms, such as butylene glycol, pentylene glycol and hexylene glycol.

The amount of the polyol to be used is held in a range of 0.01–5 w/v %, preferably 0.1–3 w/v %, and more preferably 0.5–2.5 w/v %. If the amount of the polyol to be used is excessively small, the contact lens disinfecting solution does not exhibit a synergistically improved disinfecting effect in spite of the combined use with the organic nitrogen disinfectant. On the contrary, the amount of the polyol exceeding the upper limit of 5 w/v % undesirably increases the osmotic pressure of the contact lens disinfecting solution, causing irritation to the eyes. The excessive amount of the polyol may have adverse influences especially on the soft contact lens. For instance, the size of the soft contact lens is changed to eventually change the fitting condition of the lens, resulting in deteriorated wearing comfort as felt by the lens user and lowered eyesight. Further, the eyes may suffer from irritation by the excessive amount of the polyol.

In the present contact lens disinfecting solution, the pH is adjusted to be held preferably in a range of 5–8, more preferably around 7.0, while the osmotic pressure is adjusted to be held in a range of 250–350 mOsm/kg. The pH and the osmotic pressure outside the above ranges may cause troubles such as irritation to the eyes. For adjusting the pH to be kept in the above range, a pH adjusting agent such as sodium hydroxide or potassium hydroxide is preferably used. As the tonicity agent for adjusting the osmotic pressure of the disinfecting solution to the desired value, ophthalmically acceptable inorganic salts such as sodium chloride and potassium chloride are used.

To effectively keep the pH of the contact lens disinfecting solution within the above range for assuring safety to the eyes, at least one buffer is added thereto. Any known suitable buffers may be used in the present contact lens disinfecting solution. For assuring safety to the eyes and minimizing the influence on the contact lenses, the buffer is preferably selected from among: amino acids such as citric acid, malic acid, lactic acid, ascorbic acid, maleic acid, gluconic acid, phosphoric acid, boric acid, oxycarboxylic acid, glycine and glutamic acid; acids such as tris(hydroxymethyl) aminomethane, so-called "Tris", and salts (e.g., sodium salt) thereof; Good-Buffer containing taurine and its derivatives; and hydroxyalkylamines such as bis(2-hydroxyethyl) iminotris(hydroxymethyl)methane, so-called "Bis-tris". Particularly preferably used are citric acid and salts thereof, phosphoric acid, boric acid, Good-Buffer and hydroxyalkylamines. For effectively removing the deposits derived from the tear fluid from the contact lenses, hydroxyalkylamines and Bis-tris are preferably used. The buffer is added to the present contact lens disinfecting solution generally in an amount of 0.01–2 w/v %. If the concentration of the buffer is excessively low, it is difficult to provide the intended buffering effect. The stability of the pH of the disinfecting solution does not significantly improve with an increase of the amount of the buffer above the upper limit. On the contrary, the amount of the buffer exceeding the upper limit may even cause a rise in the osmotic pressure, giving adverse influences to the eyes such as irritation.

The present contact lens disinfecting solution may further contain a nonionic surfactant for removing deposits such as eye lipid adhering to the contact lenses. It is not desirable, however, to use an anionic surfactant in the present disinfecting solution since the anionic surfactant may react with the organic nitrogen disinfectant contained therein, causing precipitation.

Any known nonionic surfactants may be used in the present invention, as long as they assure a high degree of safety to the human body without adversely affecting the material of the contact lenses. Examples of the nonionic surfactant include polyglycerin fatty acid ester, polyoxyethylene alkyl ether, polyoxyethylene-polyoxypropylene block copolymer, polyoxyethylene polyoxypropylene ethylene diamine, polyoxyethylene sorbitan fatty acid ester, condensation product of polyoxyethylene alkylphenyl ether and formaldehyde, polyoxyethylene hardened castor oil, polyoxyethylene alkylphenyl ether, polyoxyethyleneglycerin fatty acid ester, polyoxyethylene sorbitol fatty acid ester, polyoxyethylene castor oil, polyoxyethylene sterol, polyoxyethylene hydrogenated sterol, polyoxyethylene fatty acid ester, polyoxyethylene polyoxypropylene alkyl ether, polyoxyethylene lanolin alcohol, polyoxyethylene alkyl amine, polyoxyethylene alkyl amide, polyoxyethylene alkyl ether-phosphoric acid, and polysorbate.

Particularly preferably used are polyoxyethylene alkyl ether such as polyoxyethylene lauryl ether, polyoxyethylene-polyoxypropylene block copolymer of Pluronic type or Tetronic type, condensation product of polyoxyethylene alkylphenyl ether and formaldehyde such as polyoxyethylene sorbitan fatty acid ester or tiloxapol, polyoxyethylene fatty acid ester such as polyoxyethylene hardened castor oil, polyoxyethylene alkylphenyl ether or polyoxyethylene stearate, and polysorbate.

The nonionic surfactant is contained in the present contact lens disinfecting solution generally in an amount of 0.001–5 w/v %, preferably 0.005–2 w/v %, and more preferably 0.01–1 w/v %. The inclusion of the nonionic surfactant in an amount lower than 0.001 w/v % results in an insufficient cleaning effect. The cleaning effect does not improve with an increase in the amount of the nonionic surfactant above the upper limit of 5 w/v %. On the contrary, the amount of the nonionic surfactant above the upper limit may even cause eye irritation.

The present contact lens disinfecting solution may further contain a thickener as needed. It is preferable to use a nonionic or a cationic thickener which includes: gums such as heteropolysaccharide; synthetic organic high-molecular compounds such as polyvinyl alcohol, poly-N-vinyl pyrrolidone, polyethylene glycol, polypropylene glycol and polyacrylamide; and derivatives such as cellulose derivatives and starch derivatives. If the contact lenses are treated with the disinfecting solution which contains the thickener, the contact lenses can be smoothly slidable on the palm or between the fingers while the lenses are cleaned by finger-rubbing, thereby facilitating the cleaning of the contact lenses. As the thickener, the derivatives, in particular, the cellulose derivatives are preferred since the cellulose derivatives do not adversely affect the properties of the contact lenses even if the contact lenses are treated with the disinfecting solution which has been stored for a relatively long period of time. Examples of the cellulose derivatives include methyl cellulose, hydroxyethyl cellulose, hydroxypropyl cellulose, and hydroxypropylmethyl cellulose.

The present contact lens disinfecting solution may contain a chelating agent as an additional component. Any suitable chelating agents known in the art may be included as needed in the disinfecting solution, provided that they are safe to the human body, and do not adversely affect the material of the contact lenses.

For preventing metal ions such as calcium in the tear fluid from adhering to the contact lenses, especially, soft contact lenses, a metal chelating agent is preferably included in the present contact lens disinfecting solution. Examples of the metal chelating agent include: ethylenediamine tetraacetic acid (EDTA) and salts thereof such as disodium salts of ethylenediamine tetraacetic acid (EDTA.2Na), and trisodium salts of ethylenediamine tetraacetic acid (EDTA.3Na); and citric acid, gluconic acid, tartaric acid, and salts (e.g., sodium salts) of these acids. It is particularly preferable to use at least one of EDTA, EDTA.2Na and EDTA.3Na. The metal chelating agent is included generally in an amount of 0.01–2 w/v %. The excessively small amount of the metal chelating agent does not exhibit a sufficiently high chelating activity, while the excessively large amount of the metal chelating agent does not significantly enhance the chelating activity.

The contact lenses are treated with the present contact lens disinfecting solution prepared as described above, in the following manner. Initially, the contact lenses which have been removed from the eyes are cleaned by rubbing, using the present disinfecting solution. After the contact lenses are rinsed with the present disinfecting solution, the contact lenses are accommodated in a suitable container that is filled with the disinfecting solution, and stored for a predetermined time period, generally for 30 minutes or longer, preferably for 2 hours or longer. Usually, the contact lenses are soaked in the disinfecting solution overnight for disinfection. In wearing the contact lenses which has been soaked in the disinfecting solution, the contact lenses can be directly placed on the eyes without a need of rising with a physiological salt solution or saline, since the present disinfecting solution is safe to the eyes. Accordingly, the contact lenses can be cleaned, stored and disinfected by using the single disinfecting solution prepared according to the present invention, facilitating the treatment of the contact lenses.

The contact lens disinfecting solution according to the present invention can be applied to any known kinds of contact lenses such as low-water-content and high-water-content soft contact lenses, and hard contact lenses, irrespective of the materials of those contact lenses.

EXAMPLES

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention defined in the attached claims. The percentage in the following examples are on a weight/volume (w/v) basis unless otherwise specified.

Example 1

To examine the disinfecting efficacy of the present contact lens disinfecting solution, the following experiment was conducted. Initially, there were prepared specimens Nos. 1–6 of the present contact lens disinfecting solution, and a comparative specimen No. 1 of a comparative contact lens disinfecting solution, so that the specimens have the respective compositions as indicated in the following TABLE 1. These disinfecting solution specimens were prepared by using water as a medium. In these specimens, polyhexamethylene biguanide was used as the organic nitrogen disinfectant, propylene glycol (PG) was used as the polyol, “Poloxamer 407” (available from BASF JAPAN Co., Ltd., Japan) was used as the nonionic surfactant, polyvinyl alcohol (“PVA-C506” available from Kuraray Co., Ltd., Japan) was used as the cationic thickener, N,N-bis(2-hydroxyethyl)-2- aminoethanesulfonic acid (BES) was used as the buffer, and EDTA.2Na was used as the chelating agent. The pH of the disinfecting solution specimens was adjusted to be held in a range of 7.3–7.4 by using a suitable amount of sodium hydroxide as the pH adjusting agent, while the osmotic pressure of the disinfectant solution specimens was adjusted to be held in a range of 290–300 mOsm/kg by using a suitable amount of NaCl as the tonicity agent.

TABLE 1

| | Present invention | | | | | | Comparative example |
|---|---|---|---|---|---|---|---|
| composition | 1 | 2 | 3 | 4 | 5 | 6 | 1 |
| PHMB (ppm) | 1 | 1 | 1 | 1 | 1 | 0.5 | 1 |
| PG (%) | 0.5 | 1.0 | 1.5 | 1.75 | 2.0 | 2.0 | — |
| Poloxamer 407 (%) | 0.75 | 0.75 | 0.75 | 0.75 | 0.75 | 0.75 | 0.75 |
| PVA-C506 (%) | 0.50 | 0.50 | 0.50 | 0.50 | 0.50 | 0.50 | 0.50 |
| BES (%) | 0.10 | 0.10 | 0.10 | 0.10 | 0.10 | 0.10 | 0.10 |
| EDTA · 2Na (%) | 0.05 | 0.05 | 0.05 | 0.05 | 0.05 | 0.05 | 0.05 |
| NaCl (%) | 0.65 | 0.43 | 0.22 | 0.11 | — | — | 0.87 |

The thus prepared disinfecting solution specimens were evaluated of the preservative efficacy by conducting the tests according to the United States Pharmacopeia (USP) 23. In the following tests, C. a. (*Cancdida albicans* IF01594), F. s. (*Fusarium solani* ATCC36031) and S. a. (*Staphylococcus aureus* IFO13276) were used as the test bacteria or fungi. The results of the tests are indicated in the following TABLE 2 and TABLE 3.

TABLE 2

| viable cell count 4 hours after inoculation | | initial viable cell count of S. a. | initial viable cell count of C. a. |
|---|---|---|---|
| Present | | $2.3 \times 10^6$ | $8.4 \times 10^5$ |
| invention | 1 | $1.2 \times 10^3$ | $2.1 \times 10^5$ |
| | 2 | 40 | $1.4 \times 10^5$ |
| | 3 | <10 | $1.0 \times 10^5$ |
| | 5 | <10 | $5.7 \times 10^3$ |
| * | 1 | $1.5 \times 10^4$ | $3.5 \times 10^5$ |

*: comparative example

TABLE 3

| viable cell count 4 hours after inoculation | | initial viable cell count of C. a. | initial viable cell count of F. s. |
|---|---|---|---|
| Present | | $7.7 \times 10^5$ | $7.7 \times 10^5$ |
| invention | 3 | $9.8 \times 10^4$ | $6.6 \times 10^4$ |
| | 4 | $4.5 \times 10^4$ | $2.9 \times 10^4$ |
| | 5 | $6.8 \times 10^3$ | $6.6 \times 10^4$ |
| | 6 | $5.4 \times 10^4$ | $4.0 \times 10^5$ |

As is apparent from the above TABLE 2 and TABLE 3, the specimens Nos. 1–6 of the present contact lens disinfecting solution which contain the PHMB and the predetermined amounts of propylene glycol each held within the range specified in the present invention exhibited excellent disinfecting effects with respect to all of the test organisms. In contrast, the disinfecting solution specimen No.1 of the comparative example did not exhibit a sufficiently high disinfecting effect, and had a high viable cell count four hours after the inoculation. This is because the comparative specimen No. 1 did not use propylene glycol in combination with the PHMB. It will be clear that there is a striking contrast between the disinfecting effects with respect to the *S. a.* exhibited by the specimens of the present invention and the comparative specimen. In the present contact lens disinfecting solution specimens wherein the suitable organic nitrogen disinfectant (PHMB) was used in combination with the polyol (propylene glycol), the disinfecting effect of the organic nitrogen disinfectant was synergistically enhanced owing to the combined use with the polyol.

Example 2

Specimens (Nos. 7–18) of the present contact lens disinfecting solution were prepared by using water as a medium, so that the specimens had the respective compositions as indicated in the following TABLE 4 and TABLE 5. The PHMB, PG and Poloxamer 407 used in the above Example 1 were also used in this Example 2. As the buffer, one of bis(2-hydroxyethyl)iminotris(hydroxymethyl)methane, so-called "Bis-tris", tris(hydroxymethyl)aminomethane, so-called "Tris", sodium dihydrogenphosphate, boric acid, and N,N-bis(2-hydroxyethyl)-2-aminoethanesulfonic acid (BES) was used. The pH of the disinfecting solution specimens was adjusted to 7.3 by using a suitable amount of sodium hydroxide or hydrochloric acid as the pH adjusting agent, while the osmotic pressure of the specimens was adjusted to 290 mOsm/kg by using a suitable amount of NaCl as the tonicity agent.

TABLE 4

| | Present invention | | | | | |
|---|---|---|---|---|---|---|
| composition | 7 | 8 | 9 | 10 | 11 | 12 |
| PHMB (ppm) | 1 | 1 | 1 | 1 | 1 | 1 |
| PG (%) | 1.5 | 1.5 | 1.5 | 1.5 | 1.5 | 1.5 |
| Bis-tris (%) | 0.5 | — | — | — | — | — |
| Tris (%) | — | 0.5 | — | — | — | — |
| sodium dihydrogen-phosphate (%) | — | — | 0.5 | — | — | — |
| boric acid (%) | — | — | — | 0.5 | — | — |
| BES (%) | — | — | — | — | 0.5 | — |
| EDTA.2Na (%) | 0.5 | 0.5 | 0.5 | 0.5 | 0.5 | 0.5 |

TABLE 5

| | Present invention | | | | | |
|---|---|---|---|---|---|---|
| composition | 13 | 14 | 15 | 16 | 17 | 18 |
| PHMB (ppm) | 1 | 1 | 1 | 1 | 1 | 1 |
| PG (%) | 1.5 | 1.5 | 1.5 | 1.5 | 1.5 | 1.5 |
| Poloxamer 407 (%) | 0.5 | 0.5 | 0.5 | 0.5 | 0.5 | 0.5 |
| Bis-tris (%) | 0.5 | — | — | — | — | — |
| Tris (%) | — | 0.5 | — | — | — | — |
| sodium dihydrogen-phosphate (%) | — | — | 0.5 | — | — | — |
| boric acid (%) | — | — | — | 0.5 | — | — |
| BES (%) | — | — | — | — | 0.5 | — |
| EDTA · 2Na (%) | 0.5 | 0.5 | 0.5 | 0.5 | 0.5 | 0.5 |

To each of the thus prepared disinfecting solution specimens, lysozyme and albumin which are included in an FDA artificial tear solution (as specified in "Department of Health and Human Services, Food and Drug Administration: Testing Guidelines for class III Soft(Hydrophilic) Contact Lens Solution, Draft, 1985; Appendix B, pp.30") were respectively added in the concentrations of 0.02% and 0.1%, respectively. Thereafter, the appearance of each of the mixtures was inspected to evaluate the removal effect of the deposits derived from the tear fluid. Described in detail, each mixture of the disinfecting solution specimen and lysozyme or albumin was kept soaked in a thermostat held at about 90° C. for 30 minutes. Then, the mixture was taken out of the thermostat, to visually inspect its appearance. The appearance was evaluated according to the following criterion.

−: No turbidity was observed.

+: The mixture slightly turned white.

++: The mixture considerably turned white.

The results of the evaluation are indicated in the following TABLE 6.

TABLE 6

| | lysozyme-added disinfecting solution | albumin-added disinfecting liquid |
|---|---|---|
| Present invention | | |
| 7 | − | − |
| 8 | − | + |
| 9 | + | − |
| 10 | ++ | − |
| 11 | ++ | − |
| 12 | ++ | − |
| 13 | − | − |

TABLE 6-continued

| | lysozyme-added disinfecting solution | albumin-added disinfecting liquid |
|---|---|---|
| 14 | − | + |
| 15 | + | − |
| 16 | ++ | − |
| 17 | ++ | − |
| 18 | ++ | − |

As is apparent from the above TABLE 6, the disinfecting solution specimens Nos. 8–12 and 14–18 turned white due to addition of the lysozyme or the albumin thereto. It is considered that the protein denatured due to the heat or other factors was present in an insoluble state in the solution specimens which turned white. In contrast, the disinfecting solution specimens Nos. 7 and 13 which used Bis-tris as the buffer did not turn white, irrespective whether the lysozyme or albumin was added thereto. This means that the denaturation of the protein due to the heat or other factors did not occur in those solution specimens.

Since the lachrymal component includes protein such as lysozyme, it is considered that the lachrymal component is transferred onto the contact lenses, and the protein in the lachrymal component is denatured due to the heat or other factors, so that the protein becomes insoluble, eventually adhering to the lens surfaces. In the above experiments to examine the removal effect with respect to the lysozyme and albumin included in the FDA tear solution, the disinfecting solution specimens Nos. 7 and 13 which contained Bis-tris as the buffer exhibited not only a buffering effect, but also a removal effect with respect to the lysozyme and albumin, so that these disinfecting solution specimens are considered to be effective to remove the protein deposits derived from the tear fluid. In other words, if the contact lenses are treated with the disinfecting solution specimens Nos. 7 and 13, the protein deposits on the contact lenses are not denatured or coagulated due to the heat or other factors applied during the boiling of the contact lenses, whereby the protein deposits derived from the tear fluid can be easily removed from the contact lenses without adhering thereto.

Example 3

To the disinfecting solution specimen No. 13 used in the above Example 2, various thickeners shown in the following TABLE 7 were respectively added. The thus prepared disinfecting solution were evaluated of the touch or feel when the contact lenses were cleaned by finger-rubbing. The criterion of the evaluation is as follows.

◎: The contact lenses were considerably smoothly slidable on and between the fingers to such an extent that the cleaning of the contact lenses was significantly facilitated.

○: The contact lenses were sufficiently smoothly slidable.

Δ: The contact lenses were slidable.

x: The contact lenses were not smoothly slidable.

TABLE 7

| thickener | evaluation |
|---|---|
| no thickener | Δ |
| hydroxypropyl methyl cellulose (0.3 w/v %) | ◎ |
| PVA (4.0 w/v %) | ○ |
| methylcellulose (0.3 w/v %) | ◎ |

It is clear from the above TABLE 7 that the contact lenses were smoothly slidable on and between the fingers when the lenses were finger-rubbed with the disinfecting solution which included hydroxypropyl methyl cellulose as the thickener, whereby the contact lenses can be effectively cleaned owing to the enhanced cleaning capability of the disinfecting solution.

As is apparent from the above description, with the present contact lens disinfecting solution wherein the suitable organic nitrogen disinfectant is used in combination with the predetermined amount of polyol, the antimicrobial activity of the disinfectant is significantly intensified as compared when the disinfectant is used alone.

The present contact lens disinfecting solution is capable of exhibiting a sufficiently high disinfecting and preservative effect even when the amount of the disinfectant to be included therein is small enough to assure improved safety to the eyes.

Owing to the excellent disinfecting or preservative effect described above, the present contact lens disinfecting solution can be advantageously used for treating the contact lenses in each of the steps of cleaning, storing, disinfecting and rinsing the contact lenses.

What is claimed is:

1. A contact lens disinfecting solution which does not include protease, and which contains in an aqueous medium, an organic nitrogen disinfectant and 0.01–5 w/v % of at least one polyol, and further contains bis(2-hydroxyethyl)iminotris(hydroxymethyl)methane.

2. A disinfecting solution according to claim 1, which has a pH of 5–8 and an osmotic pressure of 250–350 mOsm/kg.

3. A disinfecting solution according to claim 1, wherein said at least one polyol is contained in an amount of 0.1–3 w/v %.

4. A disinfecting solution according to claim 1, wherein said at least one polyol comprises at least one of a diol and a triol which have a principal chain constituted by an alkylene group having 2–8 carbon atoms.

5. A disinfecting solution according to claim 1, wherein said at least one polyol is selected from among ethylene glycol, propylene glycol, butylene glycol, and pentylene glycol.

6. A disinfecting solution according to claim 1, wherein said organic nitrogen disinfectant comprises at least one compound selected from the group consisting of quaternary ammnonium compounds and polymerization products thereof, biguanide compounds and polymerization products thereof, and polymerization products of at least one of said quaternary ammonium compounds and at least one of said biguanide compounds.

7. A disinfecting solution according to claim 1, wherein said organic nitrogen disinfectant is contained in said aqueous medium in an amount of 0.00001–0.1 w/v %.

8. A disinfecting solution according to claim 1, further containing at least one of a nonionic surfactant, a nonionic or cationic thickener, a buffer in addition to said bis(2-hydroxyethyl)iminotris(hydroxymethyl)methane, and a chelating agent.

9. A disinfecting solution according to claim 1, containing a chelating agent and/or buffer in addition to said bis(2-hydroxyethyl)iminotris(hydroxymethyl)methane.

10. A disinfecting solution according to claim 8, wherein said buffer comprises at least one of hydroxyalkylamine and its derivatives.

11. A disinfecting solution according to claim 8, wherein said thickener comprises at least one sugar derivative.

12. A disinfecting solution according to claim 11, wherein said at least one sugar derivative comprises a cellulose derivative.

* * * * *

UNITED STATES PATENT AND TRADEMARK OFFICE

CERTIFICATE OF CORRECTION

PATENT NO. : 6,121,327
DATED : September 19, 2000
INVENTOR(S) : Akira Tsuzuki, Osamu Mori and Hideshi Nomura It is certified that error appears in the above-identified patent and that said Letters Patent is hereby corrected as shown below:

Title page,
Item [56], References Cited - Foreign Patent Documents, please add the following:

| | | |
|---|---|---|
| -- 6-321715 | 11/1994 | Japan |
| 6-504044 | 5/1994 | Japan |
| 52-110055 | 9/1977 | Japan |
| 8-224288 | 9/1996 | Japan |
| 9-38180 | 2/1997 | Japan |
| 6-194610 | 7/1994 | Japan |
| B2-2550036 | 8/1996 | Japan -- |

Signed and Sealed this

Ninth Day of October, 2001

*Attest:*

NICHOLAS P. GODICI

*Attesting Officer* *Acting Director of the United States Patent and Trademark Office*